United States Patent [19]

Dusza et al.

[11] Patent Number: 5,538,977

[45] Date of Patent: Jul. 23, 1996

[54] 3-SUBSTITUTED-7-[3-(IMIDAZOL-1-YL)-PHENYL]-PYRAZOLO[1,5-A]PYRIMIDINES

[75] Inventors: John P. Dusza; Jay D. Albright, both of Nanuet, N.Y.; Andrew S. Tomcufcik, Old Tappan, N.J.

[73] Assignee: American Cyanamid Company, Madison, N.J.

[21] Appl. No.: 413,816

[22] Filed: Mar. 17, 1995

[51] Int. Cl.$^6$ .................. C07D 239/00; A61K 31/505
[52] U.S. Cl. ............................... 514/258; 544/281
[58] Field of Search ............. 544/281; 514/257, 514/258

[56] References Cited

U.S. PATENT DOCUMENTS

| | | | |
|---|---|---|---|
| 4,178,449 | 4/1979 | Dusza et al. | 514/257 |
| 4,236,005 | 4/1980 | Dusza et al. | 514/257 |
| 4,281,000 | 5/1981 | Dusza et al. | 514/257 |
| 4,521,422 | 1/1985 | Dusza et al. | 514/257 |
| 4,576,943 | 3/1986 | Tomcufcik et al. | 514/222 |
| 4,626,538 | 10/1986 | Dusza et al. | 514/257 |
| 4,654,347 | 12/1987 | Dusza et al. | 514/257 |
| 4,900,836 | 8/1990 | Tomcufcik et al. | 546/279 |

OTHER PUBLICATIONS

T. Novinson et al., J. Med. Chem., 18(5), 460–464 (1975).
T. Novinson et al., J. Med. Chem., 17(6), 645–648 (1974).
W. E. Kirkpatrick et al., J. Med. Chem., 20(3), 386–393 (1977).
D. Martin et al., Chem. Ber., 99, 2302–2311 (1966).
M. A. Khan, J. Chem. Soc. (c), 85–91 (1970).
H. Mohler, Science, 198, 849–851 (1977).
R. F. Squires et al., Nature, 266(21), 732–734 (Apr. 1977).
J. R. Vogel et al., Psychopharmacologia, 21, 1–7 (1971).
G. Muhmel et al., Synthesis, 673–677 (1982).
R. T. Hill and D. H. Tedeschi, "Animal Testing and Screening Procedures In Evaluating Psychotropic Drugs", Intro To Psychopharm (237–288), Raven Press (1971).

*Primary Examiner*—Matthew V. Grumbling
*Attorney, Agent, or Firm*—Richard K. Jackson

[57] ABSTRACT

Disclosed are 3-substituted-7-[3-(imidazol-1-yl)phenyl]-pyrazolo[1,5-a]pyrimidines of the formula:

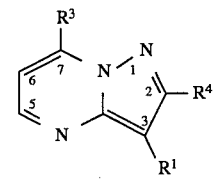

wherein $R^1$, $R^3$ and $R^4$ are defined in the specification which compounds have anxiolytic, anti-convulsant, sedative-hypnotic and skeletal muscle relaxant activity.

33 Claims, No Drawings

3-SUBSTITUTED-7-[3-(IMIDAZOL-1-YL)-PHENYL]-PYRAZOLO[1,5-A]PYRIMIDINES

BACKGROUND OF THE INVENTION

FIELD OF THE INVENTION

This invention relates to certain 3-substituted-7-[3-(imidazol-1-yl)phenyl]-pyrazolo[1,5-a]-pyrimidines which have demonstrated activity as anxiolytic or anticonvulsant agents as well as sedative-hypnotic and skeletal muscle relaxant agents.

SUMMARY OF THE INVENTION

According to the present invention, there are provided novel compounds of Formula I which have anxiolytic, anticonvulsant, sedative-hypnotic and skeletal muscle relaxant activity.

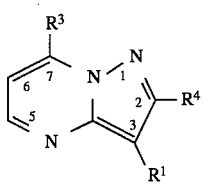

FORMULA I wherein:

$R^1$ is H, chloro, —CN and

$R^2$ is phenyl, monosubstituted phenyl, wherein the substituent is selected from halogen, alkoxy($C_1$–$C_4$), lower alkyl($C_1$–$C_4$), trifluoromethyl, alkylthio($C_1$–$C_4$), alkylamino(C1-C4), and dialkylamino($C_1$–$C_4$); thienyl, furanyl, pyridinyl; mono-substituted furanyl, thienyl, and monosubstituted pyridinyl where the substituent is selected from the group consisting of halogen, alkoxy($C_1$–$C_4$) and lower alkyl($C_1$–$C_4$);

$R^3$ is meta-substituted phenyl wherein the substituent is an imidazole moiety of the formula:

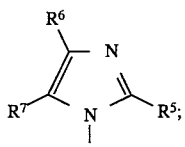

$R^5$, $R^6$ and $R^7$ are independently selected from hydrogen, methyl and ethyl with the proviso that $R^6$ cannot be methyl when $R^1$ is cyano; $R^4$ is H or $NH_2$.

The present invention also provides methods for making the novel 3-substituted-7-[3-(imidazol-1-yl)phenyl]-pyrazolo[1,5-a]-pyrimidines and methods of using the novel 3-substituted-7-[3-(imidazol-1-yl)phenyl]-pyrazolo[1,5-a] pyrimidines as anxiolytic or anticonvulsant agents as well as sedative-hypnotic and skeletal muscle relaxant agents.

DETAILED DESCRIPTION OF THE INVENTION

The preferred compounds of this invention are the compounds of Formula I wherein $R^1$ is —CN and

$R^2$ is phenyl, furanyl, thienyl, and pyridinyl; wherein $R^3$, $R^4$, $R^5$, $R^6$ and $R^7$ are as hereinbefore defined.

Most preferred compounds of this invention are the compounds of Formula I wherein $R^1$ is —CN and

$R^2$ is phenyl, furanyl, and thienyl; wherein $R^3$, $R^4$, $R^5$ $R^6$ and $R^7$ are as hereinbefore defined.

Most particularly preferred compounds of this invention are compounds of Formula I wherein $R^1$ is —CN and

$R^2$ is phenyl, furanyl, and thienyl; and $R^3$ is a meta-substituted phenyl wherein the substituent is an imidazole moiety of the formula:

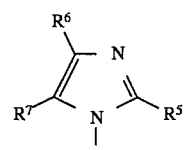

wherein $R^4$ is H or $NH_2$ and $R^5$ is H or $CH_3$ and $R^6$ and $R^7$ are hydrogen.

Additionally preferred compounds of this invention are compounds of Formula I wherein $R^1$ is —CN and

$R^2$ is phenyl, furanyl, and thienyl; and $R^3$ is a meta-substituted phenyl wherein the substituent is

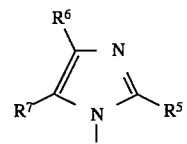

$R^4$ is H or $NH_2$; $R^6$ and $R^7$ are independently selected from hydrogen, methyl and ethyl with the proviso that $R^6$ cannot be methyl when $R^1$ is cyano.

More preferred compounds of this invention are compounds of Formula I wherein $R^1$ is:

$R^2$ is phenyl, furanyl and thienyl; wherein $R^3$, $R^4$, $R^5$, $R^6$ and $R^7$ are as hereinbefore defined.

Also preferred compounds of this invention are compounds of Formula I wherein $R^1$ is:

$R^2$ is phenyl;
wherein $R^3$, $R^4$, $R^5$, $R^6$ and $R^7$ are as hereinbefore defined.

Additionally preferred compounds of this invention are compounds of Formula I wherein $R^1$ is:

$R^2$ is furanyl;
wherein $R^3$, $R^4$, $R^5$, $R^6$ and $R^7$ are as hereinbefore defined.

More preferred compounds of this invention are compounds of Formula I wherein $R^1$ is:

$R^2$ is thienyl;
wherein $R^3$, $R^4$, $R^5$, $R^6$ and $R^7$ are as hereinbefore defined.

additionally preferred compounds of this invention are compounds of Formula I wherein $R^1$ is:

$R^2$ is phenyl, furanyl and thienyl; and $R^3$ is a meta-substituted phenyl wherein the substituent is:

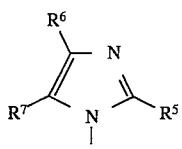

$R^4$ is H or $NH_2$; $R^5$, $R^6$ and $R^7$ are independently selected from hydrogen, methyl and ethyl with the proviso that $R^6$ cannot be methyl when $R^1$ is cyano.

The novel compounds of the present invention are prepared according to the following reaction schemes.

Scheme I

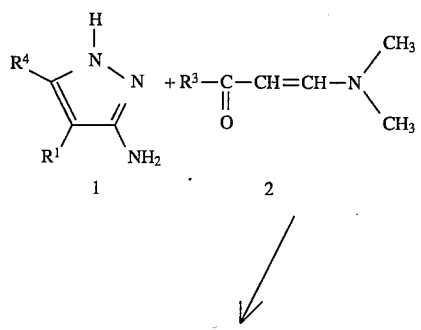

-continued
Scheme I

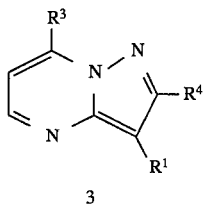

Referring to Scheme I, the reaction of the 3-amino-4-substituted pyrazole 1 where $R^1$ and $R^4$ are hereinbefore defined, and an appropriately substituted 3-dimethylamino-1-(aryl)-2-propen-1-one 2 where $R^3$ is hereinbefore defined in glacial acetic acid at reflux temperature for several hours, followed by solvent removal, partitioning of the residue between saturated aqueous sodium bicarbonate and methylene chloride, passage of the organic layer through hydrous magnesium silicate and the addition of hexane to the refluxing eluate produces the desired products 3 where $R^1$, $R^3$ and $R^4$ are hereinbefore defined.

Substituted 3-dimethylamino-1-(3-heteroaryl)2-propen-1-ones are disclosed in U.S. Pat. No. 4,281,000 and 3-dialkylaminoacrylophenones are disclosed in U.S. Pat. Nos. 4,178,449 and 4,236,005.

The 3-amino-4-pyrazoles 1 where $R^4$ is H are disclosed in one or more U.S. Pat. Nos. 4,236,005; 4,281,000; 4,521,422; 4,626,538; 4,654,347; and 4,900,836. The preparation of 3,5-diamino-1H-pyrazole-4-carbonitrile is known, see e.g. D. Martin et al., Chem. Ber., 99, 2302(1966).

Pyrazolo[1,5-a]pyrimidines are prepared by condensation of 3-aminopyrazoles and substituted 3-aminopyrazoles with 1,3-dicarbonyl compounds as described in J.Med.Chem., 18, 645(1974); J.Med.Chem.,18, 460(1975); J.Med.Chem., 20, 386(1977); Synthesis, 673(1982) and references contained therein.

As shown in Scheme II, condensation of wherein $R^3$ is hereinbefore defined and wherein Z is $-SR^{10}$, $-OR^{11}$, $-NR_8R^9$ or $-NHR^9$ wherein $R^8$ and $R^9$ are individually selected from hydrogen, alkyl($C_1-C_{10}$), phenyl and when taken together with the nitrogen atom to which they are attached form pyrrolidine, piperidine and morpholine; $R^{10}$ is alkyl($C_1-C_6$), cyclohexyl, cyclopentyl, phenyl, or $-(CH_2)_m$-phenyl where m is an integer 1–3; $R^{11}$ is hydrogen, alkyl($C_1-C_{10}$), $-(CH_2)_m$-phenyl, where m is hereinbefore defined, alkanoyl($C_2-C_{10}$), benzoyl or carboalkoxy($C_2-C_{10}$), benzoyl or carboalkoxy($C_2-C_{10}$) with the 3-amino-4-substituted pyrazole 1 where $R^1$ and $R^4$ are hereinbefore defined, produces the desired 3-substituted-7-[3-(imidazol-1-yl)phenyl]-pyrazolo[1,5-a]-pyrimidines where $R^1$, $R^3$ and $R^4$ are hereinbefore defined.

SCHEME II

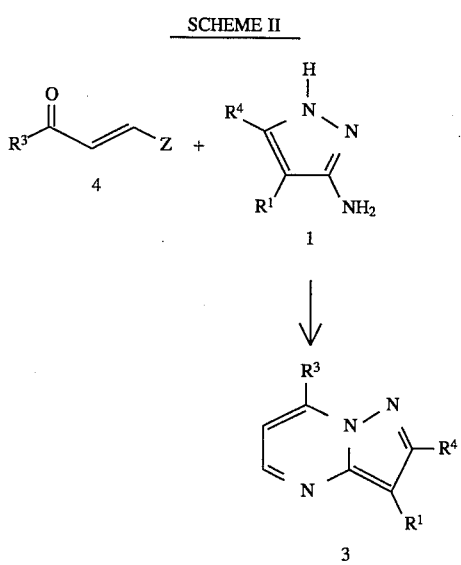

The preferred reaction conditions for condensation of hydroxymethyleneketones 4 or 3-(dialkylamino-1-aryl-2-propen-1-one 4 wherein $R^3$ is hereinbefore defined with 3-amino-pyrazoles 1 wherein $R^1$ and $R^4$ are hereinbefore defined, is by heating at 80°–130° C. in glacial acetic acid for 1–10 hours. Alternatively, the condensation reactions may be carried out with inert cosolvents in the presence of glacial acetic acid. Suitable solvents are dioxane, tetrahydrofuran, toluene, xylene, chloroform, carbon tetrachloride and the like. The novel 3-substituted-7-[3-(imidazol-1-yl)phenyl]pyrazolo[1,5-a]-pyrimidines of this invention may also be prepared by reaction of 3-amino-4-substituted pyrazole 1 with an appropriate 3-alkoxy, 3-hydroxy, 3-acetoxy, 3-alkyl-thio or 3-benzyloxy-1-aryl-2-propen-1-one 4 inert organic solvents such as lower alkanols, dioxane, tetrahydrofuran, toluene and the like at the reflux temperature thereof and with or without 1 to 10 equivalents of an acid as catalyst. Suitable acid catalysts are glacial acetic acid, hydrochloric acid, trifluoroacetic acid and the like.

The novel compounds of the present invention possess central nervous system activity at nontoxic doses and as such are useful as anxiolytic agents. That is, they produce certain responses in standard tests with laboratory animals which are known to correlate well with relief of anxiety in man. Furthermore, these compounds have been shown by biological data to be useful as sedative-hypnotic and skeletal muscle relaxant agents.

The anti-anxiety and anticonvulsant properties of the novel compounds of the present invention have been established in a test which indicates anxiolytic activity by the measure of protection from convulsions resulting from the administration of pentylenetetrazole. Single or graded dose levels of the test compounds were administered orally or intraperitoneally in a 2% starch vehicle, containing 0.5% v/v polyethylene glycol and one drop of Polysorbate 80 to groups of at least 4 rats. At 30 or 60 minutes, the rats were treated intravenously with pentylenetetrazole at a dose of 23 mg/kg of body weight. This dose is estimated to cause clonic seizures in 99% of unprotected rats. It has Been reported [R. T. Hill and D. H. Tedeschi, "Animal Testing and Screening Procedures in Evaluating Psychotropic Drugs" in "An Introduction to Psychopharmacology", Eds. R. R. Rech and K. E. Moore, Raven Press, N.Y., pp 237–288 (1971)]that there is a high degree of correlation between antagonism of pentylenetetrazole seizures in rats and anti-anxiety or anticonvulsant effects in higher warm-blooded animals. The results of this test on representative compounds of the present invention are shown in Table I.

TABLE I

Protection Against Clonic Seizures Caused By Pentylenetetrazole in Rats

| Compound (Ex. No.) | Dose (mg/Kg) | % of Rats Protected |
|---|---|---|
| 1 | 25 | 100 |
| 2 | 25 | 75 |
| 3 | 25 | 100 |
| 4 | 25 | 100 |
| 5 | 25 | 100 |
| 6 | 25 | 0 |
| 7 | 25 | 25 |
| 8 | 25 | 75 |
| 9 | 25 | 50 |
| 10 | 25 | 100 |
| 11 | 25 | 50 |
| 12 | 25 | 100 |
| 13 | 25 | 50 |
| 14 | 25 | 100 |
| 15 | 6.25 | active |
| 17 | 25 | inactive |
| 18 | NT | NT |
| 19 | 3.1 | 50 |

NT is not tested

TABLE IA

Protection Against Clonic Seizures Caused By Pentylenetetrazole in Rats

| Compound (Ex. No.) | Dose (mg/Kg) | % of Rats Protected |
|---|---|---|
| 20 | 25 | 0 |
| 21 | 25 | 0 |

Another test which has been used to assess antianxiety effects is a nonconditioned passive avoidance procedure described by [J. R. Vogel, B. Beer and D. E. Clody, "A Simple and Reliable Conflict Procedure for Testing Anti-Anxiety Agents", Psychopharmacologia, 21, 1–7(1971)]. A conflict situation is induced in rats by a modification of this method.

Groups of 6 naive, Wistar strain rats, weighing 200–240 g each were deprived of water for 48 hours and food for 24 hours. The test compounds were administered in single or graded, oral or intraperitoneal doses, suspended in a 2% starch vehicle containing 0.5% v/v polyethylene glycol and one drop of polysorbate 80. Control animals received the vehicle alone. At 30 to 60 minutes each rat was placed in an individual plexiglass chamber. Water was available ad libitum from a tap located in the rear of the chamber. A 0.7 milliampere DC shocking current was established between the stainless steel grid floor and the tap. After 20 licks of nonshocked drinking, a shock was delivered for 2 seconds and then further shocks were delivered on a ratio of one shock for 2 seconds for every 20 licks. This was continued for a total of 3 minutes. The number of shocks taken by each rat during the 3 minute interval was recorded and compared to a control group. The test compounds are considered active if the number of shocks received by the test group is significantly higher than the control group by the Mann-Witney U test. Results of this test on representative compounds of this invention appear in Table II.

TABLE II

Nonconditional Passive Avoidance Test In Rats

| EX NO | Dose (mg/Kg) | Result |
|---|---|---|
| 1 | 25 | active |
| 2 | 25 | inactive |
| 3 | 25 | active |
| 4 | 25 | inactive |
| 5 | 25 | active |
| 6 | 25 | inactive |
| 7 | 25 | active |
| 8 | 25 | active |
| 9 | 25 | active |
| 10 | 25 | active |
| 11 | 25 | inactive |
| 12 | 25 | active |
| 13 | 25 | active |
| 14 | 25 | active |
| 15 | 25 | active |
| 17 | 25 | active |
| 18 | 25 | NT |
| 19 | 25 | active |

NT is not tested

TABLE IIA

Nonconditional Passive Avoidance Test in Rats

| (Ex. No.) | Dose (mg/Kg) | Result |
|---|---|---|
| 20 | 25 | inactive |
| 21 | 25 | inactive |

Another test utilized for the determination of anxiolytic activity is the measurement of the ability of test compounds to inhibit the binding of tritiated benzodiazepines to brain-specific receptors of warm-blooded animals. A modification of the method described by R. F. Squires, et al., Nature, 266, No. 21, p. 732 (April, 1977) and H. Mohler, et al., Science, 198, p. 849(1977) was employed.

Male albino rats (Wistar strain, weighing 150–200 g each) are obtained from Royalhart Farms. $^3$H-diazepam (79.9 Ci/mmol) and 3H-flunitrazepam (84.3 Ci/mmol) are obtained from New England Nuclear. The test compounds are solubilized in either dimethylformamide, acetic acid, ethanol or hydrochloric acid.

Whole cortex of rats is homogenized gently in 20 volumes of ice-cold 0.32M sucrose, centrifuged at 30,000 g for 20 minutes to produce a crude $P_2$-synaptosomal fraction. The $P_2$-fraction was either: (1) resuspended in twice the original volume in hipotonic 50 mM Tris.HCl (pH 7.4), or (2) resuspended in one-half the original volume in hypotonic 10 mM Tris.HCl (pH 7.4) and frozen (–20° C.) until time of use. Frozen $P_2$ preparations are thawed and resuspended in four times the original homogenizing volume at time of assay.

The binding assay consisted of 300 μl of the $P_2$-fraction suspension (0.2–0.4 mg protein), 100 μl of test drug and 100 μl of 3H-diazepam (1.5 nM, final concentration) or 3H-flunitrazepam (1.0 nM, final concentration) which was added to 1.5 ml of 50 nM Tris.HCl (pH 7.4). Nonspecific binding controls and total binding controls received 100 μl of diazepam (3 JIM, final concentration) and 100 μl of deionized water, respectively, in place of the test compound. Incubation for 30 minutes proceeded in ice and was terminated by filtration, under vacuum, through Whatman GF/C glass fiber filters. The filters were washed twice with 5 ml of ice-cold 50 mM Tris.HCl (pH 7.4) and placed in scintillation vials. After drying at 50°–60° C. for 30 minutes, 10 ml of Beckman Ready-Solv TM HP (a high performance premix scintillation cocktail, registered trademark of Beckman instruments, Inc., Irvine, Calif. 92713) was added and the radioactivity determined in a scintillation counter.

Inhibition of binding was calculated by the difference between total binding and binding in the presence of test compound, divided by the total binding, ×100.

The results of this test on representative compounds of the present invention are given in Table III.

TABLE III

Inhibition of the Binding of $^3$H-Benzodiazepine to Brain-Specific Receptors of Rats

| Ex No. | % Inhibition |
|---|---|
| 1 | 98 |
| 2 | 88 |
| 3 | 44 |
| 4 | 94 |
| 5 | 72 |
| 6 | 72 |
| 7 | 101 |
| 8 | 75 |
| 9 | 98 |
| 10 | 99 |
| 11 | 100 |
| 12 | NT |
| 13 | NT |
| 14 | 93 |
| 15 | 98 |
| 17 | 90 |
| 18 | NT |
| 19 | NT |

NT is not tested

TABLE IIIA

Inhibition of the Binding of $^3$H-Benzodiazepine to Brain-Specific Receptors of Rats

| Ex. No. | % Inhibition |
|---|---|
| 20 | NT |
| 21 | inactive |

The novel compounds of the present invention have been found to be highly useful for meliorating anxiety, treating convulsions, inducing sedation or hypnosis and inducing skeletal muscle relaxation in mammals when administered in amounts ranging from about 0.1 mg to about 20.0 mg/kg of body weight per day. A preferred dosage regimen for optimum results would be from about 0.5 mg to about 10.0 mg/kg of body weight per day. Such dosage units in association with a pharmaceutically acceptable carrier are employed that a total of from about 10 to about 700 mg of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of nonvolatile, normally liquid, polyethylene glycols which are soluble in both water and organic liquids and which have molecular weight of from about 200 to 1500. Although the amount of active compound dissolved in the above vehicle may vary from 0.10% to 10.0% by weight, it is preferred that the amount of active compound employed be from about 3.0 to about 9.0% by weight. Although various mixtures of the aforementioned nonvolatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg/ml of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg/ml of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food or the diet. For oral therapeutic administration, the active compounds may be incorporated with excipients and used in the form of tablets, troches, capsules, elixirs, suspensions, syrups, wafers, and the like. Additionally, the active ingredient may be incorporated with the proper pharmaceutical carrier or carriers known in the art to produce a sustained-release tablet or capsule. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain one or more of the following: a binder such as gum tragacanth, acacia, corn starch or gelatin; excipients such as dicalcium phosphate; a disintegrating agent such as corn starch, potato starch, alginic acid and the like, a lubricant such as magnesium stearate; a wetting agent such as sodium lauryl sulfate and a sweetening agent such as sucrose, lactose or saccharin may be added or a flavoring agent such as peppermint, oil of wintergreen, or cherry flavoring. When the dosage unit form is capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially nontoxic in the amounts employed.

The invention will be further described by the following nonlimiting examples.

Reference Example 1

3'-(1-Imidazolyl)acetophenone

A mixture of 25 g of 3'-bromoacetophenone, 9.0 g of imidazole, 18 g of anhydrous potassium carbonate, 1.0 g of copper oxide (CuO) and 30 ml of pyridine is refluxed for 64 hours. The mixture is cooled to room temperature, filtered and the filter cake washed with 50 ml of pyridine and 3×50 ml of dichloromethane. The combined filtrates are concentrated to dryness under vacuum. The residue is partitioned between 250 ml of dichloromethane and 150 ml of water. The emulsion is clarified by filtration through a pad of diatomaceous earth. The organic layer is separated, dried (MgSO$_4$) and filtered through a pad of hydrous magnesium silicate. The pad is washed with 50 ml of dichloromethane and the combined filtrate is concentrated on a steam bath to 150 ml and while hot 300 ml of hexane is added. The mixture is cooled to room temperature, activated carbon added and the mixture filtered through diatomaceous earth. The filtrate is cooled to −10° C. and filtered to give 3.6 g of crystals, mp 69°–71° C. The filtrate is treated with activated carbon, filtered and the filtrate evaporated to give 12 g of crystals, mp 62°–65° C.

The following Reference Examples (Table IV) are prepared according to the above procedure for Reference Example 1. The general procedure is described by M. A. Khan and J. B. Polya, *J.Chem.Soc.*(C), 85(1970).

TABLE IV

| Reference Example | Name | m.p. |
|---|---|---|
| 2 | 1-[3-(2-methyl-1H-imidazol-1-yl)phenyl]ethanone | 105–107° |
| 3 | 1-[3-(4-methyl-1H-pyrazol-1-yl)phenyl]ethanone | 75–78° |
| 4 | 1-[3-(2-ethyl-1H-imidazol-1-yl)phenyl]ethanone | |

Reference Example 5

3-(Dimethylamino)-1-[3-(1H-imidazol-1-yl)phenyl-2-propen-1-one

A mixture of 25.0 g of 3'-(1-imidazolyl)acetophenone and 25 ml of dimethylformamide dimethylacetal under argon is heated on a steam bath for 12 hours. The volatiles are removed under reduced pressure to give 27.24 g of a solid. The solid is dissolved in dichloromethane and passed through a short column of hydrous magnesium silicate. The column is washed with several volumes of dichloromethane as eluent. The filtrate is refluxed on a steam bath while hexane is gradually added. When crystals begin to form, the solution is removed from the steam bath and chilled, filtered and the solid washed with hexane to give 21.8 g of product as crystals, mp 125°–128° C.

The following Reference Examples (Table V) are prepared according to the procedure of Reference Example 5.

TABLE V

| Reference Example | Name | m.p. |
|---|---|---|
| 6 | 3-(Dimethylamino)-1-[3-(2-methyl-1H-imidazol-1-yl)-phenyl]-2-propen-1-one | 136–137° C. |
| 7 | 3-(Dimethylamino)-1-[3-(4-methyl-1H-imidazol-1-yl)-phenyl]-2-propen-1-one | 134–136° C. |
| 8 | 1-[3-(2-Ethyl-1H-imidazol-1-yl)-phenyl]-3-(dimethylamino)-2-propen-1-one | 146–148° |

Example 1

[7-[3-(2-Methyl-1H-imidazol-1-yl)phenyl]pyrazolo-[1,5-a]pyrimidin-3-yl]phenylmethanone compound with dichloromethane (20:1;)

A solution of 0.37 mol of 3-amino-4-benzoylpyrazole and 0.50 mol of 3-(dimethylamino)-1-[3-(2-methyl)-4-imidazol-1-yl)phenyl]-2-propen-1-one in 25 ml of glacial acetic acid is refluxed for 6 hours and then evaporated to dryness. The residue is partitioned between saturated aqueous sodium bicarbonate and methylene chloride. The methylene chloride solution is dried over powdered anhydrous sodium sulfate and then the solution is passed through a short column of hydrous magnesium silicate. The filtrate is boiled on a steam bath with the addition of hexanes until crystallization is noted. After cooling the product is recovered by filtration and air drying to give 0.47 g of the desired product as a solid, mp 159°–160° C. The NMR indicates a trace of methylene chloride. Calcd for $C_{23}H_{17}N_5O \cdot 0.05\ CH_2Cl_2$ (383.657):C, 72.16; H,4.49; N,18.25. Found C,71.91; H,4.38;N,18.21.

Following the procedure of Example 1 and using the appropriate reactants, the products of Example 2–21 found in Table VI are obtained.

TABLE VI

| Ex No. | Pyrazole | 3-Dimethylamino-1-substituted-2-alken-1-one | Product | M.P. °C. |
|---|---|---|---|---|
| 2 | 3-amino-4-pyrazole-carbonitrile | 3-(dimethylamino)-1-[3-(2-methyl-1H-imidazol-1-yl)-phenyl]-2-propen-1-one | 7-[3-(2-methyl-1H-imidazol-1-yl)-phenyl]pyrazolo[1,5-a]pyrimidine-3-carbonitrile compd. with dichloromethane 20:1 | 259–260 |
| 3 | 3-amino-4-pyrazole-carbonitrile | 4'-(1-imidazolyl)-3-dimethylamino-acrylophenone | 7-[3-(1H-imidazol-1-yl)phenyl]-pyrazolo[1,5-a]pyrimidine-3-carbonitrile | 287–290° C. |
| 4 | (3-amino-1H-pyrazol-4-yl)(phenyl)-methanone | 4'-(1-imidazolyl)-3-dimethylamino-acrylophenone | [7-[3-(1H-imidazol-1-yl)phenyl]pyrazolo[1,5-a]pyrimidin-3-yl]phenylmethanone | 220–222° C. |
| 5 | (3-amino-1H-pyrazol-4-yl)(2-furanyl)-methanone | 3-(dimethylamino)-1-[3-(1H-imidazol-1-yl)phenyl-2-propen-1-one | 2-furanyl[7-[3-(1H-imidazol-1-yl)-phenyl]-pyrazolo-[1,5-a]pyrimidin-3-yl]methanone | 242–244° C. |
| 6 | 3-aminopyrazole | 3-(dimethylamino)-1-[3-(1H-imidazol-1-yl)phenyl-2-propen-1-one | 7-[3-(1H-imidazol-1-yl)-phenyl]pyrazolo[1,5-a]pyrimidine | 177–179° C. |
| 7 | (3-amino-1H-pyrazol-4-yl)(2-furanyl)-methanone | 3-(dimethylamino)-1-[4-(2-methyl-1H-imidazol-1-yl)-phenyl]-2-propen-1-one | 2-furanyl[7-[3-(2-methyl-1H-imidazol-1-yl)phenyl]pyrazolo[1,5-a]pyrimidin-3-yl]methanone compd. with dichloromethane (100:3) | 153–155° C. |
| 8 | (3-amino-1H-pyrazol-4-yl)(2-thienyl)-methanone | 3-(dimethylamino)-1-[3-(4-methyl-1H-imidazol-1-yl)-phenyl]-2-propen-1-one | [7-[3-(4-methyl-1H-imidazol-1-yl)-phenyl]pyrazolo[1,5-a]pyrimidin-3-yl]-2-thienyl-methanone | 232–234° C. |
| 9 | (3-amino-1H-pyrazol-4-yl)-(2-furanyl)-methanone | 3-(dimethylamino)-1-[4-(2-methyl-1H-imidazol-1-yl)-phenyl]-2-propen-1-one | 2-furanyl[7-[3-(4-methyl-1H-imidazol-1-yl)phenyl]pyrazolo[1,5-a]pyrimidin-3-yl]methanone | 199–200° C. |

TABLE VI-continued

| Ex No. | Pyrazole | 3-Dimethylamino-1-substituted-2-alken-1-one | Product | M.P. °C. |
|---|---|---|---|---|
| 10 | (3-amino-1H-pyrazol-4-yl)-(2-thienyl)-methanone | 3-(dimethylamino)-1-[4-(2-methyl-1H-imidazol-1-yl)-phenyl]-2-propen-1-one | [7-[3-(2-methyl-1H-imidazol-1-yl)-phenyl]pyrazolo[1,5-a]pyrimidin-3-yl]-2-thienyl-methanone compd. with dichloromethane (20:1) | 172–174° C. |
| 11 | (3-amino-1H-pyrazol-4-yl)-(2-thienyl)-methanone | 4'-(1-imidazolyl)-3-dimethylamino-acrylophenone | [7-[3-(1H-imidazol-1-yl)phenyl]pyrazolo[1,5-a]pyrimidin-3-yl]-2-thienyl-methanone | 242–244° C. |
| 12 | 3-amino-4-chloro-pyrazole | 3-(dimethylamino)-1-[3-(4-methyl-1H-imidazol-1-yl)-phenyl]-2-propen-1-one | 3-chloro-7-[3-(2-methyl-1H-imidazol-1-yl)phenyl]pyrazolo[1,5-a]pyrimidine compd. with dichloromethane (20:1) | 247–249° C. |
| 13 | 3-aminopyrazole | 3-(dimethylamino)-1-[3-(4-methyl-1H-imidazol-1-yl)-phenyl]-2-propen-1-one | 7-[3-(2-methyl-1H-imidazol-1-yl)-phenyl]pyrazolo[1,5-a]pyrimidine | 158–160° C. |
| 14 | (3-amino-1H-pyrazol-4-yl)-(phenyl)-methanone | 3-(dimethylamino)-1-[3-(4-methyl-1H-imidazol-1-yl)-phenyl]-2-propen-1-one | [7-[3-(4-methyl-1H-imidazol-1-yl)-phenyl]pyrazolo[1,5-a]pyrimidin-3-yl]-phenylmethanone compd. with dichloromethane (20:1) | 185–186° C. |
| 15 | (3-amino-1H-pyrazol-4-yl)-(phenyl)-methanone | 1-[3-(2-ethyl-1H-imidazol-1-yl)-phenyl]-3-(dimethylamino)-2-propen-1-one | [7-[3-(2-ethyl-1H-imidazol-1-yl)-phenyl]pyrazolo[1,5-a]pyrimidin-3-yl]-phenylmethanone | 133–135° C. |
| 16 | (3-amino-1H-pyrazol-4-yl)-(phenyl)-methanone | 3-(dimethylamino)-1-[4-(2-methyl-1H-imidazol-1-yl)-phenyl]-2-propen-1-one | [7-[4-(2-methyl-1H-imidazol-1-yl)-phenyl]pyrazolo[1,5-a]pyrimidin-3-yl]-phenylmethanone | 228–230° C. |
| 17 | 3-(amino-1H-pyrazol-4-yl)(4-pyridinyl)-methanone | 3-(dimethylamino)-1-[3-(1H-imidazol-1-yl)phenyl]-2-propen-1-one | [7-[3-(1H-imidazol-1-yl)-phenyl]pyrazolo[1,5-a]pyrimidin-3-yl]-4-pyridinylmethanone | 253–255° C. |
| 18 | (3-amino-1H-pyrazol-4-yl)(3-thienyl)-methanone | 3-(dimethylamino)-1-[3-(1H-imidazol-1-yl)phenyl]-2-propen-1-one | [7-[3-(1H-imidazol-1-yl)-phenyl]pyrazolo[1,5-a]pyrimidin-3-yl]-3-thienyl-methanone | 225–226° C. |
| 19 | 3,5-diamino-1H-pyrazole-4-carbonitrile | 3-(dimethylamino)-1-[3-(2-methyl-1H-imidazol-1-yl)-phenyl]-2-propen-1-one | 2-amino-7-[3-(2-methyl-1H-imidazol-1-yl)phenyl]pyrazolo-[1,5-a]pyrimidine-3-carbonitrile monohydrochloride | 340–345° C. |
| 20 | 3-amino-4-pyrazole carbonitrile | 3-(dimethylamino)-1-[3-(4-methyl-1H-imidazol-1-yl)-phenyl]-2-propen-1-one | 7-[3-(4-methyl-1H-imidazol-1-yl)-phenyl]pyrazolo-[1,5-a]pyrimidine-3-carbonitrile | 275–280° C. |
| 21 | ethyl 3-amino-4-pyrazole carboxylate | 3-(dimethylamino)-1-[3-(2-methyl-1H-imidazol-1-yl)-phenyl]-2-propen-1-one | ethyl 7-[3-(2-methyl-1H-imidazol-1-yl)phenyl]pyrazolo[1,5-a]pyrimidine-3-carboxylate | 160–163° C. |

We claim:

1. A compound of the formula:

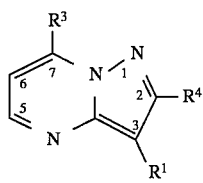

wherein:

$R^1$ is H, chloro, —CN or

$R^2$ is phenyl, mono-substituted phenyl, wherein the substituent is selected from halogen, alkoxy($C_1$–$C_4$), lower alkyl($C_1$–$C_4$), trifluoromethyl, alkylthio($C_1$–$C_4$), alkylamino($C_1$–$C_4$), and dialkylamino($C_1$–$C_4$); thienyl, furanyl, pyridinyl; mono-substituted furanyl, mono-substituted thienyl, or monosubstituted pyridinyl where the substituent is selected from the group consisting of halogen, alkoxy($C_1$–$C_4$) and lower alkyl($C_1$–$C_4$);

$R^3$ is meta-substituted phenyl wherein the substituent is an imidazole moiety of the formula:

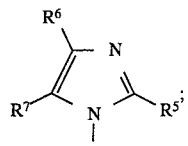

$R^5$, $R^6$ and $R^7$ are independently selected from hydrogen, methyl and ethyl with the proviso that $R^6$ cannot be methyl when $R^1$ is cyano; $R^4$ is H or $NH_2$.

2. A compound according to claim 1 wherein $R^1$ is —CN or

and $R_2$ is phenyl, furanyl, thienyl, or pyridinyl.

3. A compound according to claim 1 wherein $R^1$ is —CN or

and $R^2$ is phenyl, furanyl, or thienyl.

4. A compound according to claim 1 wherein $R^1$ is —CN or

$R^2$ is phenyl, furanyl, or thienyl; and $R^3$ is a meta-substituted phenyl wherein the substituent is

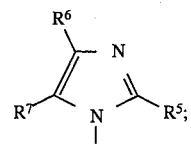

$R^4$ is H or $NH_2$; $R^5$ is H or $CH_3$; $R^6$ or $R^7$ are hydrogen.

5. A compound according to claim 1 wherein $R^1$ is —CN or

$R^2$ is phenyl, furanyl, or thienyl; and $R^3$ is a meta-substituted phenyl wherein the substituent is

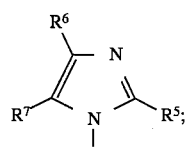

$R^4$ is H or $NH_2$; $R^5$, $R^6$ or $R^7$ are independently selected from hydrogen, methyl or ethyl with the proviso that $R^6$ cannot be methyl when $R^1$ is cyano.

6. A compound according to claim 1 wherein $R^1$ is

and $R^2$ is phenyl, furanyl, or thienyl.

7. A compound according to claim 1 wherein $R^1$ is

and $R^2$ is phenyl.

8. A compound according to claim 1 wherein $R^1$ is

and $R^2$ is furanyl.

9. A compound according to claim 1 wherein $R^1$ is

and $R^2$ is thienyl.

10. A compound according to claim 1 wherein $R^1$ is

$R^2$ is phenyl, furanyl, or thienyl; and

R³ is a meta-substituted phenyl wherein the substituent is

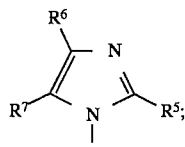

R⁴ is H or NH₂; R⁵, R⁶ or R⁷ are independently selected from hydrogen, methyl or ethyl with the proviso that R⁶ cannot be methyl when R¹ is cyano.

11. The compound according to claim 1, [7-[3-(2-methyl-1H-imidazol-1-yl)phenyl]pyrazolo[1,5-a]pyrimidin-3-yl]phenylmethanone.

12. The compound according to claim 1, 7-[3-(2-methyl-1H-imidazol-1-yl)phenyl]pyrazolo[1,5-a]pyrimidine-3-carbonitrile.

13. The compound according to claim 1, 7-[3-(1H-imidazol-1-yl)phenyl]-pyrazolo[1,5-a]pyrimidine-3-carbonitrile.

14. The compound according to claim 1, [7-[3-(1H-imidazol-1-yl)phenyl]pyrazolo[1,5-a]pyrimidin-3-yl]phenylmethanone.

15. The compound according to claim 1, 2-furanyl[7-[3-(1H-imidazol-1-yl)phenyl]pyrazolo[1,5-a]pyrimidin-3-yl]methanone.

16. The compound according to claim 1, 7-[3-(1H-imidazol-1-yl)-phenyl]pyrazolo[1,5-a]pyrimidine.

17. The compound according to claim 1, 2-furanyl[7-[3-(2-methyl-1H-imidazol-1-yl)phenyl]pyrazolo[1,5-a]pyrimidin-3-yl]methanone.

18. The compound according to claim 1, [7-[3-(4-methyl-1H-imidazol-1-yl)phenyl]pyrazolo[1,5-a]pyrimidin-3-yl]-2-thienylmethanone.

19. The compound according to claim 1, 2-furanyl[7-[3-(4-methyl-1H-imidazol-1-yl)phenyl]pyrazolo[1,5-a]pyrimidin-3-yl]methanone.

20. The compound according to claim 1, [7-[3-(2-methyl-1H-imidazol-1-yl)phenyl]pyrazolo[1,5-a]pyrimidin-3-yl]-2-thienylmethanone.

21. The compound according to claim 1, [7-[3-(1H-imidazol-1-yl)phenyl]pyrazolo[1,5-a]pyrimidin-3-yl]2-thienylmethanone.

22. The compound according to claim 1, 3-chloro-7-[3-(2-methyl-1H-imidazol-1-yl)phenyl]pyrazolo[1,5-a]pyrimidine.

23. The compound according to claim 1, 7-[3-(2-methyl-1H-imidazol-1-yl)phenyl]pyrazolo[1,5-a]pyrimidine.

24. The compound according to claim 1, [7-[3-(4-methyl-1H-imidazol-1-yl)phenyl]pyrazolo[1,5-a]pyrimidin-3-yl]phenylmethanone.

25. The compound according to claim 1, [7-[3-(2-ethyl-1H-imidazol-1-yl)phenyl]pyrazolo[1,5-a]pyrimidin-3-yl]phenylmethanone.

26. The compound according to claim 1, [7-[3-(1H-imidazol-1-yl)-phenyl]pyrazolo[1,5-a]pyrimidin-3-yl]-4-pyridinylmethanone.

27. The compound according to claim 1, [7-[3-(1H-imidazol-1-yl)-phenyl]pyrazolo[1,5-a]pyrimidin-3-yl]-3-thienylmethanone.

28. The compound according to claim 1, 2-amino-7-[3-(2-methyl-1H-imidazol-1-yl)phenyl]pyrazolo[1,5-a]pyrimidine-3-carbonitrile monohydrochloride.

29. A method of meliorating anxiety in a mammal suffering from anxiety which comprises administering to said mammal an effective anxiolytic amount of a compound of claim 1.

30. A method of treating convulsions in a mammal suffering from convulsions which comprises administering to said mammal an effective anticonvulsant amount of a compound of claim 1.

31. A method of inducing sedation or hypnosis in a mammal which comprises administering to said mammal an effective sedative or hypnotic amount of a compound of claim 1.

32. A method of inducing skeletal muscle relaxation in a mammal which comprises administering to said mammal an effective skeletal muscle relaxant amount of a compound of claim 1.

33. A composition of matter in dosage unit form comprising from 10 to 700 mg of a compound of claim 1 in association with a pharmaceutically acceptable carrier.

* * * * *